United States Patent
Bian et al.

(10) Patent No.: US 9,427,503 B2
(45) Date of Patent: Aug. 30, 2016

(54) CARDIOTOMY SUCTION TUBE SYSTEM WITH MULTIPLE TIPS

(71) Applicants: Xiaoming Bian, Dalian (CN); Frank Zheng, Kirkland, WA (US)

(72) Inventors: Xiaoming Bian, Dalian (CN); Frank Zheng, Kirkland, WA (US)

(73) Assignee: Corvivo Inc., Coquitlam, British Columbia (CA)

( * ) Notice: Subject to any disclaimer, the term of this patent is extended or adjusted under 35 U.S.C. 154(b) by 0 days.

(21) Appl. No.: 13/837,080

(22) Filed: Mar. 15, 2013

(65) Prior Publication Data

US 2014/0276486 A1    Sep. 18, 2014

(51) Int. Cl.
| | |
|---|---|
| *A61M 1/00* | (2006.01) |
| *A61M 25/00* | (2006.01) |
| *A61M 39/22* | (2006.01) |
| *A61M 1/36* | (2006.01) |

(52) U.S. Cl.
CPC ........... *A61M 1/0031* (2013.01); *A61M 1/008* (2013.01); *A61M 1/0039* (2013.01); *A61M 1/0041* (2013.01); *A61M 39/223* (2013.01); *A61M 1/3659* (2014.02); *A61M 1/3666* (2013.01)

(58) Field of Classification Search
CPC ........... A61M 1/3692; A61M 1/0281; A61M 1/0039; A61M 1/0041; A61M 1/0043; A61M 1/0047; A61M 1/008; A61M 2005/14; A61M 2005/165; A61M 2202/0413; A61M 1/3621; A61M 1/3627; Y10S 261/28
USPC ........................................ 604/540, 541, 544
See application file for complete search history.

(56) References Cited

U.S. PATENT DOCUMENTS

| | | | |
|---|---|---|---|
| 1,236,865 A * | 8/1917 | Pittenger | 604/258 |
| 4,205,677 A | 6/1980 | Engstrom | |
| 4,285,341 A * | 8/1981 | Pollack | A61M 25/00 604/28 |
| 4,654,036 A * | 3/1987 | Tolkoff | 604/270 |
| 4,658,655 A * | 4/1987 | Kanno | 73/863.85 |
| 4,681,564 A * | 7/1987 | Landreneau | 604/128 |
| 4,863,424 A * | 9/1989 | Blake et al. | 604/524 |
| 4,886,487 A | 12/1989 | Solem et al. | |
| 5,423,769 A * | 6/1995 | Jonkman et al. | 604/250 |
| 5,458,582 A * | 10/1995 | Nakao | 604/264 |
| 5,813,842 A * | 9/1998 | Tamari | 417/477.1 |
| 5,891,111 A * | 4/1999 | Ismael | 604/541 |
| 6,001,078 A | 12/1999 | Reekers | |
| 6,254,591 B1 * | 7/2001 | Roberson | 604/541 |
| 6,423,268 B1 * | 7/2002 | King et al. | 422/44 |
| 6,547,755 B1 | 4/2003 | Lippe et al. | |
| 6,547,777 B2 * | 4/2003 | DiResta et al. | 604/506 |
| 6,733,433 B1 * | 5/2004 | Fell | 494/37 |

(Continued)

FOREIGN PATENT DOCUMENTS

| | | |
|---|---|---|
| EP | 0158037 A1 | 10/1985 |
| EP | 1731181 A1 | 12/2006 |

*Primary Examiner* — Adam Marcetich
(74) *Attorney, Agent, or Firm* — Inskeep IP Group, Inc.

(57) ABSTRACT

A cardiotomy suction tube system comprises a main line, a first flexible branch line in fluid communication with the main line, a second flexible branch line in selective fluid communication with the main line, and a rigid branch line in selective fluid communication with the main line. A valve mechanism selectively places either the second flexible branch line or the rigid line in fluid communication with the main line. The first flexible branch line may be provided with a weighted suction tip which gravitates to a low point in an operative field. The second flexible branch line may be provided with a weighted suction tip which gravitates to a low point in an operative field.

10 Claims, 2 Drawing Sheets

(56) References Cited

U.S. PATENT DOCUMENTS

Figure 1:
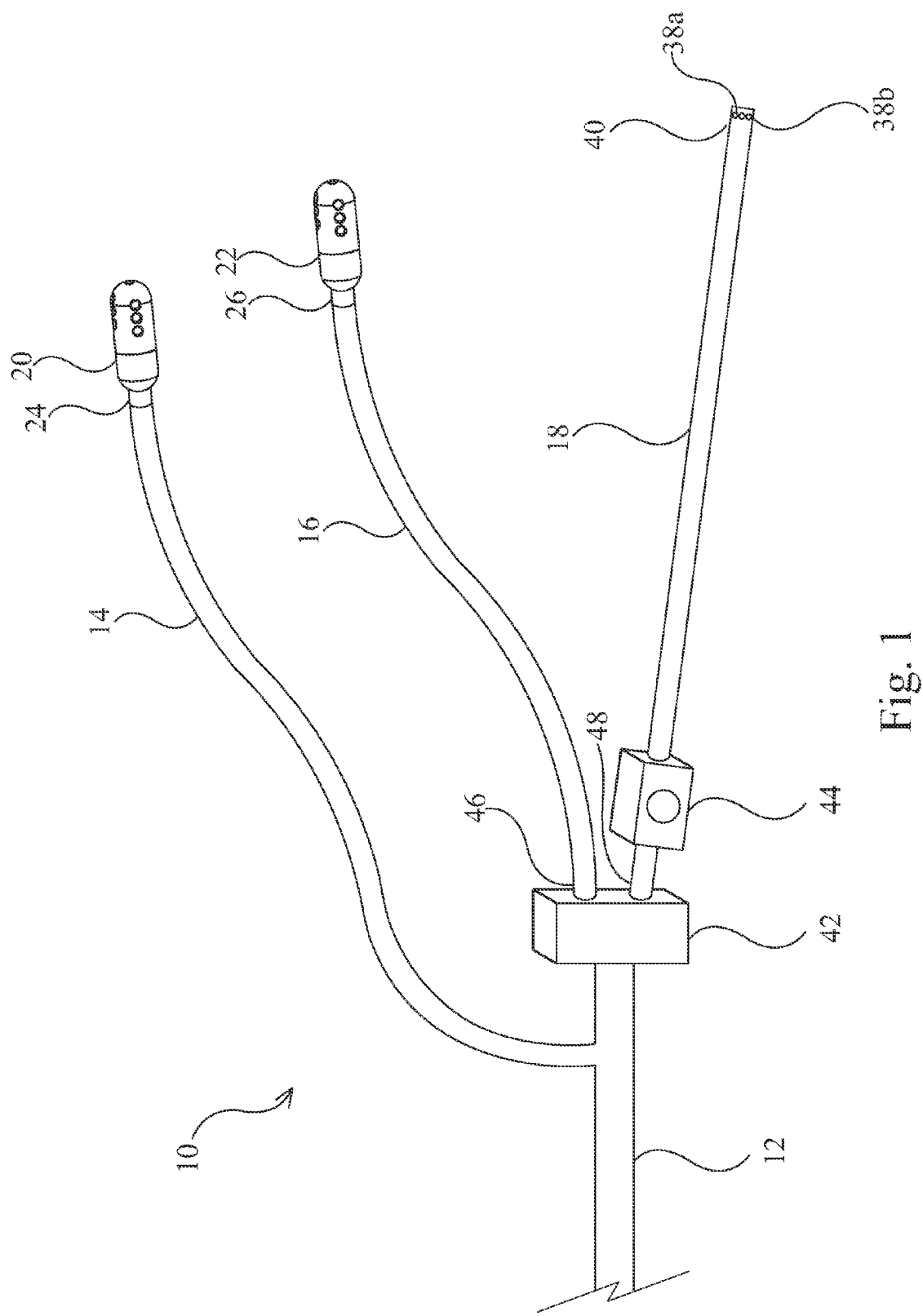

| | | |
|---|---|---|
| 2006/0100605 A1* | 5/2006 | Bicakci et al. ............... 604/540 |
| 2006/0155249 A1* | 7/2006 | Hishikawa et al. .......... 604/252 |
| 2007/0016136 A1* | 1/2007 | Opie ............................ 604/119 |
| 2009/0030270 A1* | 1/2009 | Arai et al. ..................... 600/37 |
| 2009/0054823 A1* | 2/2009 | Bridges et al. .............. 604/6.09 |
| 2010/0324483 A1* | 12/2010 | Rozenberg .......... A61M 16/045 <br> 604/98.01 |
| 2011/0132482 A1* | 6/2011 | Honma et al. ................ 137/605 |
| 2012/0078220 A1* | 3/2012 | Fallin et al. .................. 604/500 |
| 2012/0095537 A1* | 4/2012 | Hall et al. .................... 607/105 |
| 2013/0131616 A1* | 5/2013 | Locke .......................... 604/321 |

\* cited by examiner

CARDIOTOMY SUCTION TUBE SYSTEM WITH MULTIPLE TIPS

BACKGROUND OF THE INVENTION

1. Field of the Invention

The present invention relates to a suction tube system and, in particular, to a cardiotomy suction tube system with multiple tips.

2. Description of the Related Art

It is known to use cardiotomy suction systems to reduce blood in the operative field during open surgical operations. A conventional cardiotomy suction system is disclosed in U.S. Pat. No. 4,205,677 which issued on Jun. 3, 1980 to Engstrom. The cardiotomy suction system disclosed by Engstrom comprises a cardiotomy suction tube provided with a tip. The tip is placed in the operative field and blood is drawn into the cardiotomy suction tube. The rate that blood is drawn from the operative field into the cardiotomy suction tube is controlled by a valve block. A surgeon is able to selectively control the rate that blood is drawn from field of surgery by actuating the valve block.

However, conventional cardiotomy suction systems such as the type disclosed by Engstrom may be limited because they are generally only provided with a single card iotomy suction tube with a single tip. Since a single cardiotomy suction tube may also not be sufficient to adequately remove blood from the operative field, thereby necessitating the use of a plurality of cardiotomy suction systems during surgical operations. It may also be necessary to switch back and forth between a flexible tip and a rigid tip during the same surgical operations.

SUMMARY OF THE INVENTION

There is provided a cardiotomy suction tube system comprising a main line, a flexible branch line in selective fluid communication with the main line, and a rigid branch line in selective fluid communication with the main line. A valve mechanism selectively places either the flexible branch line or the rigid branch line in fluid communication with the main line. The flexible branch line may be provided with a weighted suction tip which gravitates to a low point in an operative field.

There is also provided a cardiotomy suction tube system comprising a main line, flexible branch lines in fluid communication and selective fluid communication with the main line, and a rigid branch line in selective fluid communication with the main line. The flexible branch lines are hand-free suction lines and the rigid branch line is hand-hold suction line. A valve mechanism selectively places one of the flexible branch lines or the rigid branch line in fluid communication with the main line to selectively have only one of the said flexible branch line and the rigid branch line in fluid communication with the main line. The flexible branch lines may be provided with a weighted suction tip which gravitates to a low point in an operative field.

There is further provided a cardiotomy suction tube system comprising a main line, a first branch line in fluid communication with the main line, a second branch line in selective fluid communication with the main line, and a third branch line in selective fluid communication with the main line. A valve mechanism selectively places either the second branch line or the third branch line in fluid communication with the main line. The first branch line may be flexible. The second branch line may be flexible. The third branch line may be substantially rigid. The first branch line may be provided with a weighted suction tip which gravitates to a low point in an operative field. The second branch line may be provided with a weighted suction tip which gravitates to a low point in an operative field. There may be a vacuum release mechanism disposed along the third branch line.

BRIEF DESCRIPTIONS OF DRAWINGS

Figure 2:
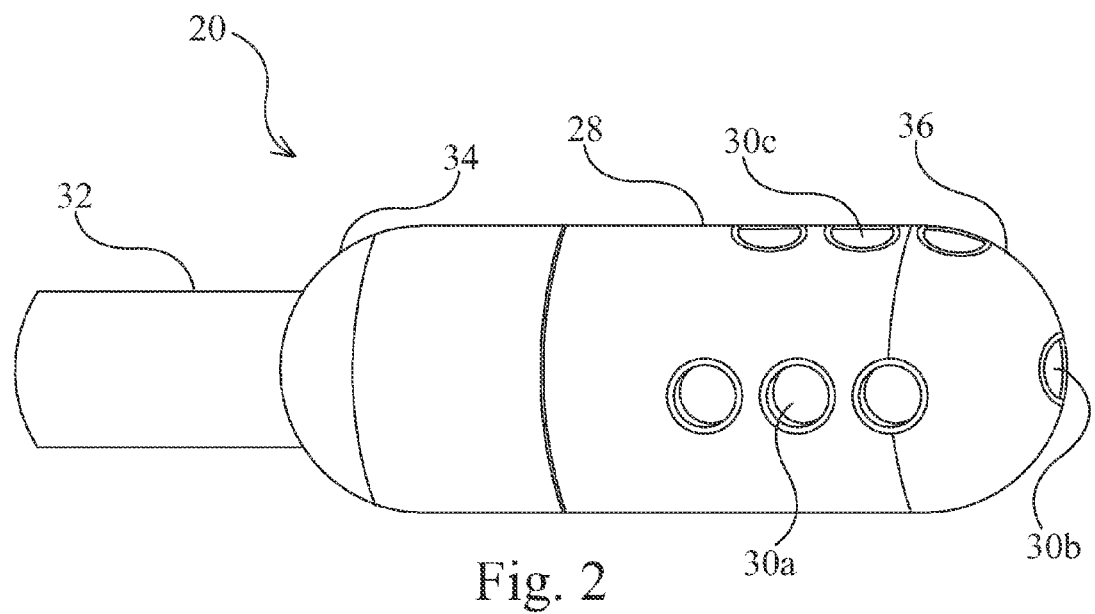

The invention will be more readily understood from the following description of the embodiments thereof given, by way of example only, with reference to the accompanying drawings, in which:

FIG. 1 is a fragmentary, perspective view of an improved cardiotomy suction tube system; and FIG. 2 is a perspective view of a tip of the cardiotomy suction tube system shown in FIG. 1.

DESCRIPTIONS OF THE PREFERRED EMBODIMENTS

Referring to the drawings and first to FIG. 1, an improved suction tube system 10 is shown. The suction tube system 10 generally comprises a main line 12, which is shown in fragment, and a plurality of branch lines 14, 16 and 18. The first and second branch lines 14 and 16 are flexible while the third branch line 18 is substantially rigid. The first branch line 14 and the second branch line 16 are each provided with a respective suction tip 20 and 22 at a distal end 24 and 26 thereof.

The suction tip 20 of the first branch line 14 is shown in greater detail in FIG. 2. The suction tip 20 has a hollow body 28 with a plurality of apertures, for example apertures 30a, 30b and 30c, which allow fluid communication between the surrounding environment and an interior of the hollow body 28. The suction tip 20 also has a cylindrical projection 32 which extends outwardly from hollow body 28. The cylindrical projection 32 may receive or may be received by the first branch line 14 and thereby couples the suction tip 20 to the first branch line as shown in FIG. 1.

Referring back to FIG. 2, in this example, the hollow body 28 of the suction tip 22 is generally capsule shaped and is elongate with rounded ends 34 and 36. The cylindrical projection 32 extends longitudinally of the hollow body 28 from one of the rounded ends 34 thereof. It will be understood by a person skilled in the art the suction tip 22, shown in FIG. 1, of the second branch line 16 has a substantially similar structure and functions in a substantially similar manner as the suction tip 20 of the first branch line 14. The third branch line 18 does not have a separate suction tip in this example. However, the third branch line is provided with a plurality of apertures, for example apertures 38a and 38b, which allow fluid communication between the surrounding environment and an interior of the third branch line 18. In this example, the apertures 38a and 38b are disposed near a distal end 40 of the third branch line 18.

The suction tube system 10 further includes a three-way valve mechanism 42 and a vacuum release mechanism 44. The second branch line 16 and the third branch line 18 are each connected to the three-way valve at their respective proximal ends 46 and 48. Accordingly, while the first branch line 14 should always be in fluid communication with the main line 12, the second branch line 16 and the third branch line 18 may selectively be placed in fluid communication with the main line 12. For example, the second branch line 16 may be in fluid communication with the main line 12 while the third branch line 18 is closed to the main line 12. Likewise, the third branch line 18 may be in fluid communication with the main line 12 while the second branch line 16 is closed to the main line 12. The vacuum release mechanism 44 is disposed along the third branch line 18. The vacuum release mechanism 44 is a switch which may be actuated to allow or block negative pressure in the third branch line 18. The vacuum release mechanism 44 may be actuated block negative pressure in the third branch line 18 when the apertures 38a and 38b of the third branch line 18 are blocked by tissue.

The suction tube system 10 disclosed herein provides the advantage of having at least two lines, namely, the first branch line 14 and one of the second branch line 16 and the third branch line 18, drawing fluid when the suction tube system 10 is in use. In this example, the first branch line 14 and the second branch line 16 are made of from a soft medical grade material such as rubber or silicone while their respective suction tips 20 and 22 are made from a weighted material such as metal or are loaded with a weight. The weighted suction tips 20 and 22 gravitate towards the lowest point of an operative field where blood generally pools. The ability to selectively have either the second branch line 16 or the third branch line 18 in fluid communication with the main line 12 allows a surgeon to easily switch back and forth between a flexible branch line and a rigid branch line during cardiovascular surgery. The rigid branch line may be made of metals, metal alloys, hard plastics, or polymers.

It will be understood by a person skilled in the art that although the suction tube disclosed herein is described for use as a cardiotomy suction tube that the suction tube may be used in other applications.

It will also be understood by a person skilled in the art that many of the details provided above are by way of example only, and are not intended to limit the scope of the invention which is to be determined with reference to the following claims.

What is claimed is:

1. A cardiotomy suction tube system consisting essentially of:
    a main suction line;
    a first branch suction line in direct and continuous fluid communication with the main suction line;
    a second branch suction line in selective fluid communication with the main suction line;
    a third branch suction line in selective fluid communication with the main suction line; and
    a three-way valve mechanism to selectively place either the second branch suction line or the third branch suction line in fluid communication with the main suction line, the second branch suction line and the third branch suction line each being connected to the three-way valve mechanism at their respective proximal ends; wherein the first branch suction line and the second branch suction line each have a distal tip configured to draw fluid from an operative field and the third branch suction line has a distal end configured to draw fluid from the operative field.

2. The cardiotomy suction tube system as claimed in claim 1 wherein the first branch suction line and the second branch suction line are flexible, and the third branch suction line is substantially rigid.

3. The cardiotomy suction tube system as claimed in claim 1 wherein the first branch suction line is flexible and the second branch suction line is provided with a weighted suction tip which gravitates to a low point in an operative field.

4. The cardiotomy suction tube system as claimed in claim 1 wherein the second branch suction line is flexible and the first branch suction line is provided with a weighted suction tip which gravitates to a low point in an operative field.

5. The cardiotomy suction tube system as claimed in claim 1 further including a vacuum release mechanism disposed along the third branch suction line.

6. A cardiotomy suction tube system consisting essentially of:
    a main suction line;
    a first flexible branch suction line in direct and continuous fluid communication with the main suction line;
    a second flexible branch suction line in selective fluid communication with the main suction line;
    a rigid branch suction line in selective fluid communication with the main suction line; and
    a three-way valve mechanism to selectively place either the second flexible branch suction line or the rigid branch suction line in fluid communication with the main suction line, the second flexible branch suction line and the rigid branch suction line each being connected to the three-way valve mechanism at their respective proximal ends; wherein the first flexible branch suction line and the second flexible branch suction line each have a distal tip configured to draw fluid from an operative field and the rigid branch suction line has a distal end configured to draw fluid from the operative field.

7. The cardiotomy suction tube system as claimed in claim 6 wherein the first flexible branch suction line is provided with a weighted suction tip which gravitates to a low point in an operative field.

8. The cardiotomy suction tube system as claimed in claim 6 wherein the second flexible branch suction line is provided with a weighted suction tip which gravitates to a low point in an operative field.

9. A cardiotomy suction tube system consisting essentially of:
    a main suction line;
    a flexible branch suction line in selective fluid communication with the main suction line;
    a rigid branch suction line in selective fluid communication with the main suction line; and
    a three-way valve mechanism to selectively place either the flexible branch suction line or the rigid branch suction line in fluid communication with the main suction line, the flexible branch suction line and the rigid branch suction line each being connected to the three-way valve mechanism at their respective proximal ends; wherein the flexible branch suction line has a distal tip configured to draw fluid from an operative field and the rigid branch suction line has a distal end configured to draw fluid from the operative field.

10. The cardiotomy suction tube system as claimed in claim 9 wherein the flexible branch suction line is provided with a weighted suction tip which gravitates to a low point in an operative field.

* * * * *